United States Patent [19]

Gilchrist et al.

[11] Patent Number: 5,780,438

[45] Date of Patent: *Jul. 14, 1998

[54] DIALYSIS FLUID CONTAINING PEPTIDES OBTAINED FROM CASEIN AS OSMOTIC AGENTS AND BICARBONATE IONS AS BUFFERING AGENTS AND PHYSIOLOGICAL SALTS

[75] Inventors: Thomas Gilchrist, Ayr; William Manson, Strathclyde, both of Scotland

[73] Assignee: Giltech Limited, Ayr, Scotland

[*] Notice: This patent issued on a continued prosecution application filed under 37 CFR 1.53(d), and is subject to the twenty year patent term provisions of 35 U.S.C. 154(a)(2).

[21] Appl. No.: 605,049

[22] PCT Filed: Jun. 2, 1995

[86] PCT No.: PCT/GB95/01275

§ 371 Date: Mar. 7, 1996

§ 102(e) Date: Mar. 7, 1996

[87] PCT Pub. No.: WO95/33477

PCT Pub. Date: Dec. 14, 1995

[30] Foreign Application Priority Data

Jun. 2, 1994 [GB] United Kingdom .................. 941009

[51] Int. Cl.$^6$ ..................................................... A61K 37/18
[52] U.S. Cl. .................. 514/21; 514/2; 514/12
[58] Field of Search ....................... 514/2, 21, 12

[56] References Cited

U.S. PATENT DOCUMENTS

| | | | |
|---|---|---|---|
| 4,906,616 | 3/1990 | Gilchrist et al. | 514/21 |
| 4,959,175 | 9/1990 | Yatzidis | 252/364 |
| 5,039,609 | 8/1991 | Klein | 435/68.1 |

FOREIGN PATENT DOCUMENTS 0 277 868  8/1988  European Pat. Off. .

OTHER PUBLICATIONS

Martis, L. et al. "Experimental peritoneal dialysis solutions" Peritoneal Dialysis International, vol. 13, suppl. 2, 1993, pp. S98–S100.

A.J. Hutchison et al. "Improved solutions for peritoneal dialysis: physiological . . . " Kidney International, vol. 42, Suppl 38 (1992), pp. S–153–S–159.

E. Klein et al., "Peptides as substitute osmotic agents for glucose . . . " ASAIO Trans., 1986, vol. 32, pp. 550–553.

*Primary Examiner*—Chhaya D. Sayala
*Attorney, Agent, or Firm*—Nixon & Vanderhye

[57] ABSTRACT

The invention discloses fluids for use in medical dialysis procedures which contain proteolytic hydrolysates of one or more proteins (e.g. casein) as effective osmotic agent and bicarbonate ions as buffering agent. Additionally the dialysis fluid contains physiological salts.

16 Claims, No Drawings

DIALYSIS FLUID CONTAINING PEPTIDES OBTAINED FROM CASEIN AS OSMOTIC AGENTS AND BICARBONATE IONS AS BUFFERING AGENTS AND PHYSIOLOGICAL SALTS

This invention is concerned with a fluid for use in medical dialysis procedures and particularly, although not exclusively, in peritoneal dialysis as employed in the technique of Continuous Ambulatory Peritoneal Dialysis (CAPD).

In the human body, solutes transfer from one body fluid to another by diffusion processes which include dialysis, osmosis and ultrafiltration (hereafter referred to collectively simply as "dialysis"). Unwanted solutes, toxins and excess water are transferred from the bloodstream by dialysis in the kidneys for excretion from the body. In the event of kidney malfunction, the indicated medical treatment is usually kidney transplantation or, alternatively, extracorporeal haemodialysis. The preferred treatment is transplantation but this depends on the availability of donor kidneys of compatible tissue type. The surgical procedure is lengthy, and therefore expensive in manpower and equipment costs and, although controllable to a great extent by drug administration, rejection of the transplanted kidney may occur. Transplantation, however, remains the preferred treatment as the patients may thereafter lead a more or less normal lifestyle.

Haemodialysis is a substitute for kidney transplantation. Depending on the severity of the renal malfunction, patients require more or less frequent sessions of dialysis. Blood is withdrawn from the patient's bloodstream and passed through a dialyser wherein the blood is brought into contact with a selectively permeable membrane, made for example, of cellulosic or synthetic polymeric material, the remote side of which contacts a dialysis fluid. By the laws of diffusion, solutes in the blood are transported across the membrane into the dialysis fluid and water is removed by ultrafiltration.

Haemodialysis is normally carried out under medical supervision in the out-patients department of hospitals, although it can be done by the patient at home should he or she be capable of scrupulous observation of procedures after training. The absence of suitable conditions in the home or inability of the patient for one reason or another to observe the rules of procedure may preclude home dialysis. Dialysis machines are expensive and require a substantial amount of maintenance by way of routine sterilisation.

Haemodialysis is extremely restricting to the patient. For example, if leaving the vicinity of the treatment centre he or she has to make arrangements to be treated at a dialysis unit in the locality of his or her destination. In summary, renal dialysis is an extremely restricting form of treatment to the patient who has to attend hospital for dialysis and it requires a great deal of patient cooperation and attention to procedural details if it is to be carried out at home. The hardware associated with the procedure is also expensive.

Peritoneal dialysis is now a well-established procedure which may be used as a substitute for extracorporeal haemodialysis for those patients for whom, because of some medical condition other than the renal failure itself, the use of haemodialysis is contra-indicated or is simply not available.

In peritoneal dialysis, a dialysis fluid is introduced via a catheter into the peritoneal cavity in the abdomen of the patient and removal of toxins and water takes place across the peritoneum which acts as the semi-permeable membrane. The peritoneal cavity is flooded with the fluid, left for an appropriate lapse of time, and then drained.

In Continuous Ambulatory Peritoneal Dialysis (CAPD), a catheter is permanently implanted by surgery through the abdomen wall of the patient and it is through the catheter that the dialysis liquid is introduced, commonly, because procedures are simple, by the patient himself or herself from a flexible sachet of the sterile fluid. Once the fluid has been introduced, the patient simply rolls up the attached sachet, stores it still attached to the catheter in a pocket in his or her clothing, and is then free to continue normal activity while dialysis takes place. Later, he or she drains the spent fluid under gravity back into the sachet for disposal and introduces a fresh batch. Thus, dialysis is continuous and this has the advantage over periodic sessions of dialysis that intermittent disruption of the body chemistry of the patient is avoided. The frequency of change of the fluid varies from patient to patient but may be about four times in each twenty-four hour period.

In any form of dialysis the dialysis fluid should desirably contain physiological ions in concentrations which are substantially isotonic. In tis way undesirable loss of physiological ions can be minimised and the risk of damage to the patient's membranes and blood cells through imposition of too great an osmotic pressure can likewise be minimised. Amongst such physiological ions there can be mentioned $Na^-$, $Mg^{2+}$, $Ca^{2+}$ and $Cl^-$. In a dialysis fluid having an osmolality of, for example, about 300 mOsm/Kg, the physiological salts may be responsible for approximately 250 mOsm/Kg.

In addition to physiological salts it is also usual to include in a dialysis fluid an effective osmotic agent which provides the additional osmolality necessary to cause the unwanted substances, such as urea, to cross the dialysis membrane, whether this is the membrane of a renal dialysis machine or the patient's peritoneum, from the patient's blood stream. Care must be taken in selecting such an effective osmotic agent in order that not too high an osmotic pressure is set up across the dialysis membrane. Moreover it should be non-toxic in case of leakage through the dialysis membrane and not have an adverse effect upon the patient in case it crosses the dialysis membrane. Desirably it should have a sufficiently high molecular weight that diffusion through the dialysis membrane is reduced as far as possible, but not so high that very high concentrations thereof by weight are necessary in the dialysis fluid to produce the desired osmolality.

Saccharides, glucose being the most common, are often included in the dialysis fluid to impart the necessary osmotic gradient. Almost any substance which is introduced into the peritoneal cavity will find its way eventually into the bloodstream and this passage is increased by the presence of breaks in the integrity of the peritoneal membrane, a condition which is not uncommon in patients who require the treatment. While the body may be quite capable of metabolising additional sugar, the long term effect of including saccharides in a dialysis fluid is undesirable and in certain patients, such as diabetics, constitutes an unacceptable medical hazard, and may require the additional complication of the patient having to introduce insulin into the dialysis fluid.

It has also been previously proposed to use, as the effective osmotic agent, oligo- and poly-saccharides. However, should these materials penetrate through the peritoneal membrane, hydrolysis may occur resulting in depolymerisation and the same unacceptable condition associated with simple sugars arises. Substances such as sorbitol, sylitol, polyglucoses and fructose have been investigated for application in peritoneal dialysis but have not been found wide acceptance.

It has also been proposed to add various polymers, including sodium salts of synthetic polypeptides and proteins containing at least 10 mole percent of aspartic acid, glutamic acid, or a combination thereof. This proposal is described in U.S. Pat. No. 4,339,433. Large amounts of such high molecular weight materials would be needed to achieve the necessary osmality.

An alternative approach is to include glycerol in a dialysis fluid as the effective osmotic agent. This approach is disclosed in WO-A-82/83987. However, the glycerol molecule is rather small and tends to pass readily through the dialysis membrane. Its presence in a dialysis solution is undesirable when patients suffering from diabetes are being treated.

Amino acid mixtures are widely used in medicine for the treatment of diverse medical conditions and appear to have potential for use as osmotic agents in dialysis fluids. They are non-toxic and are well tolerated by the body but, being of low molecular weight and size, they tend to penetrate the peritoneal membrane very easily and so rapidly that loss of the osmotic gradient can occur resulting in reverse flow of solutes from the dialysis fluid into the circulation. However, previous work on this subject has established the non-toxicity of these substances.

Protein hydrolysate solutions, which can, for example, be obtained by enzymatic hydrolysis of casein, are used for injection in certain medical indications. They can be modified by partial removal or restoration or addition of one or more amino acids. They may contain alcohol, dextrose or other carbohydrate suitable for intravenous injection.

U.S. Pat. No. 4,906,616 relates to a dialysis fluid containing, as an effective agent for maintaining the osmalality of the fluid, a protein hydrolysate resulting from the action of a proteolytic enzyme on the sodium caseinate fraction of milk protein.

In renal insufficiency, metabolic acidosis is one of the problems which dialysis seeks to solve. For this purpose, dialysis solutions incorporate a buffering material, which in CAPD fluid was initially bicarbonate (Boen, S. T., *Peritoneal Dialysis in Clinical Medicine*, C. C. Thomas, Springfield, Ill., USA, 1964, p45). However, bicarbonate-containing glucose-based fluids were found to give rise to precipitates, within the peritoneum, of calcium carbonate and magnesium carbonate. In addition, peritoneal dialysis solutions containing bicarbonate, calcium, magnesium and glucose are extremely difficult to prepare, sterilise and store (Biasioli, S. et al., Sodium Lactate and other buffers for dialysis, *Contemporary Dialysis*, 10, 46, 1982), due to formation of insoluble salts and interaction of glucose and bicarbonate during autoclaving. Bicarbonate can be replaced as buffer by lactate and occasionally by acetate. However, it is generally accepted that metabolic acidosis cannot be fully corrected by the 35 mmol/l lactate solutions normally employed in CAPD. Furthermore, both lactate and acetate have been reported to produce side-effects and metabolic difficulties (Biasoli, S. et al., Buffers in peritoneal dialysis, *Journal of Artificial Organs*, 10, 3–8, 1987). The same authors suggested that the low pH of solutions containing glucose, which is necessary to avoid caramelisation of the glucose during autoclaving, together with the accompanying unphysiological concentrations of lactate, could damage the peritoneal membrane with unwanted consequences for the patient.

If only sodium bicarbonate could be delivered to the patient without risk of precipitation of insoluble carbonates with the peritoneum, it would be the ideal buffering agent in CAPD.

Numerous attempts have been made over the past 10 years to achieve this. These have without exception involved the location of the glucose dialysis solution in a chamber in a dialysis bag separated from a solution of sodium bicarbonate in a second chamber of the bag by a thin partition. Immediately before use the partition is breached and the solutions mixed within the bag producing a bicarbonate-buffered glucose dialysis fluid. While this solution is claimed to be effective in correction of uraemic acidosis (Feriani, M. et al., Continuous ambulatory peritoneal dialysis with bicarbonate buffer—a pilot study, *Peritoneal Dialysis International* 13 (Suppl.2) 588–91, 1993), procedures of this type are regarded as somewhat unwieldy and not convenient in a practical sense for chronic treatment. Furthermore, the manufacture of such systems is more complicated than for the preparation of a fluid in a single-chambered bag. Procedures of this kind are clearly less than ideal but are at present a necessary consequence of obtaining the considerable advantages associated with replacing lactate with bicarbonate as a buffering agent in glucose-based dialysis fluids.

It is an object of the present invention to provide a dialysis fluid which does not suffer from the aforesaid limitations. It is a further object to provide a bicarbonate buffered dialysis fluid, suitable for use in CAPD, which does not deposit precipitates of magnesium or calcium bicarbonate or carbonate on storage.

Accordingly, the present invention provides a dialysis fluid comprising:

i) an effective osmotic agent which comprises one or more peptides obtainable by the action of a proteolytic enzyme on a protein or mixture of proteins, and ii) a buffering agent which comprises bicarbonate ions.

In one embodiment of the invention, the protein or mixture of proteins comprises casein. It is usually convenient to use bovine casein in this regard. Other protein sources such as egg albumin or whey proteins may also be used in the proteins or protein mixtures from which the peptides used in the dialysis fluids of the invention are obtained.

Casein is readily available in large quantities. A suitable grade is food grade casein. This is normally produced from milk, preferably from bovine milk. In solution at a pH of 7.0 or greater it is present as sodium caseinate, assuming that pH adjustment is effected with, for example, sodium hydroxide. It is a mixture of phosphoproteins, each of whose structures has, in the case of bovine casein, been fully elucidated. Consequently, upon treatment of casein or sodium caseinate with a proteolytic enzyme having a high specificity of activity, such as trypsin, a mixture of peptides which contains a predictable pattern of molecular sizes is formed, due to the enzyme having cleaved the protein at the relevant sites susceptible to enzymatic attack. Typically, when trypsin is used as proteolytic enzyme, the peptide mixture has a theoretical average molecular weight of about 1000 daltons, a value confirmed by exclusion chromatography. The peptide mixture contains some small peptide fragments having molecular weights in the range of from about 250 to about 500 daltons, and a few larger fragments with molecular weights of from about 1800 to about 3000 daltons. The larger fragments can be removed, if desired, by precipitation in the pH range 4.5–5.1. The smaller fragments which amount to <10% of the total peptide content are not separated from the main peptide fraction having an average molecular weight of about 1000. A further reduction in average molecular weight can be achieved by enzymatic hydrolysis with a second proteolytic enzyme, such as chymotrypsin. Again, membranes can be used to screen out molecules larger than or smaller than the desired size.

Preferably the concentration of bicarbonate ions in the dialysis fluid is from 20–40 meq/l.

Amongst the proteolytic enzymes which may be used to form the peptide mixture which is included in the dialysis fluids of the invention are trypsin, chymotrypsin, pancreatin, pronase or combinations thereof. A mixture of two or more enzymes may be used to form a peptide mixture from the selected protein, e.g. casein. Alternatively two or more enzymes can be used in turn, with or without removal of the first added enzyme prior to addition of the second enzyme.

Generally a dialysis fluid according to the invention will have an osmolality of from about 100 to about 400 mOsm/Kg, preferably about 250 to about 350 mOsm/Kg. The effective osmotic agent typically contributes from about 25 to about 100 mOsm/Kg to the total osmolality, the balance being typically provided by physiological salts.

The pH of a dialysis fluid according to the invention is generally from about 6.6 to about 7.6.

The dialysis fluids of the invention contain sufficient of the effective osmotic agent, in addition to any physiologically acceptable salts, to impart to the fluid an osmalality of from about 25 to about 100 mOsm/Kg. Besides the peptides obtainable or obtained by proteolytic enzymatic action on a protein, such as casein, the dialysis fluid may further include a minor amount of another osmotic agent, such as, for example, glucose or glycerol. Such minor further osmotic agents typically impart from 0 to about 5 mOsm/Kg in total to the osmolality of the dialysis fluid.

Preferably, the dialysis fluids of the invention will be substantially free from glucose and glycerol. It will be appreciated that the dialysis fluids disclosed herein may further contain physiological salts comprising ions selected from sodium, calcium, chloride, lactate, citrate and magnesium.

The use of the peptide mixtures derived from bovine casein by the action of proteolytic enzymes such as, for example, trypsin along or trypsin followed by chymotrypsin, as effective osmotic agent in place of glucose has rendered possible the formulation of stable dialysis fluids containing bicarbonate. These solutions can have any particular desired pH value within the physiological range and most notably between 6.6 and 7.6. They can also accommodate $Na^+$, $Mg^{2+}$, $Ca^{2+}$ and $Cl^-$ in the concentrations normally encountered in CAPD, preferably in substantially isotonic amounts. No lactate is required since it is typically replaced in the dialysis fluid of the invention by 33–35 meq/l bicarbonate. The unwelcome side-effects and metabolic difficulties associated with the use of lactate alluded to above are avoided by use of this bicarbonate-containing fluid. This represents a significant advantage over the glucose-based fluids known in the art.

Fluids prepared as described below and containing peptides, $HCO_3^-$, $Cl^-$, $Na^+$, $Ca^{2+}$ and $Mg^{2+}$ in concentrations suitable for use in CAPD have shown no precipitations in vitro when stored at near 20° C. and pH 7.2 for several months. The lack of precipitation is ascribed to chemical properties of the peptides which are present in quantities sufficient to solubilise the constituent $Ca^{2+}$ and $Mg^{2+}$ ions.

The procedure for the preparation of bicarbonate-containing peptide-based fluids according to the invention may be described, by way of illustration, as follows.

EXAMPLE 1

Commercially available food grade bovine acid casein, 80 g, was suspended in pyrogen-free water, 900 ml at 30° C., and 3M-sodium hydroxide was added dropwise with stirring in such a way that the pH never exceeded 7.5. When solution of the protein was completed and the pH had been finally adjusted to pH7.5, crystalline trypsin, 320 mg, dissolved in 0.001M-hydrochloric acid, 30 ml was added. The mixture was maintained at a temperature of 30° C. and using a glass electrode the pH was monitored and maintained at 7.5 by addition of 3M-sodium hydroxide to neutralise acid liberated by the action of trypsin on the casein. The hydrolysis was complete in around two hours. At this stage, crystalline chymotrypsin, 320 mg, dissolved in 0.001M-hydrochloric acid, 30 ml, was added and the reaction mixture maintained at 30° C. and pH 7.5 for a further two hours. Thereafter the pH was reduced to 4.6 by gradual addition of 3M-hydrochloric acid. After standing overnight at 20° C. during which time a small flocculent precipitate appeared, the mixture was clarified by filtration. The solution in turn was subjected to filtration through a polysulphone membrane with a stated capability of retaining molecules having molecular weight values in excess of 10000 after which a second filtration through a polysulphone membrane having a cut-off of 5000 was performed. The resulting peptide mixture comprised peptides in the molecular weight range 300 to 1000 daltons, the average molecular weight of the peptide mixture being in the region of from about 700 to about 800 daltons. This range of values was confirmed by mass spectroscopy. It was enzyme-free.

To the solution thus obtained was added sufficient 3M-sodium hydroxide solution to bring the pH to 6.7 after which were added physiological amounts of $Na^+$, $Ca^{2+}$, $Mg^{2+}$, $Cl^-$ and $HCO_3^-$ as follows: $Na^+$ 130–145 m.equiv/liter; $Ca^{2+}$ 1.5–2.5 m.equiv/liter; $Cl^-$ 90–110 m.equiv/liter; $HCO_3^-$/30–35 m.equiv/liter; and $Mg^{2+}$ zero–2.0 m.equiv/liter. The pH of the resulting solution was adjusted to a desired pH within the range 7.0–7.5 by dropwise addition of 3M-sodium hydroxide solution. The osmolality was close to 300 mOsm/Kg, typically in the range of from about 303–352 mOsm/Kg, of which around 245–305 mOsm/Kg, typically around 252–299 mOsm/Kg, can be ascribed to the salts and approximately 50 mOsm/Kg to the peptide mixture.

The contribution to total osmolality provided by the peptide mixture can be reduced by dilution with water at an appropriate point in the preparation of increased by use of a stronger casein solution initially.

This solution was sterilised by filtration through a microporous bacterial filter of pore size 0.2 microns. The resulting solution was sterile and free from both pyrogens and residual enzyme activity.

Preliminary in vivo tests were performed on non-uraemic laboratory rats in which the above solution was injected into the peritoneal cavity. No ill-effects were observed in the rats. The solution was neither toxic nor immunogenic and was an effective dialysis agent.

EXAMPLE 2

Commercially available food grade bovine casein, 80 g, was subjected to proteolytic degradation exactly as described in Example 1 above, except that treatment with chymotrypsin was omitted. The fluid obtained differed from that produced in Example 1 only in respect of the average molecular weight of its constituent peptides which in this instance was approximately 1000 daltons, compared with 700–800 daltons in Example 1. Samples of this fluid containing bicarbonate produced no visible precipitation after storage at ambient temperature for up to three years.

We claim:

1. A dialysis fluid which is stable upon storage without precipitation and which comprises:
   i) an osmotic agent which comprises a mixture of peptides obtained by the action of a proteolytic enzyme on a protein source selected from casein and whey proteins,
   ii) a buffering agent which comprises bicarbonate ions; and
   iii) at least one cation selected from the group consisting of Ca2+ and Mg2+.

2. A dialysis fluid according to claim 1, wherein the protein source comprises casein.

3. A dialysis fluid according to claim 2, wherein the casein comprises bovine casein.

4. A dialysis fluid according to claim 1, wherein the proteolytic enzyme comprises trypsin, chymotrypsin, pancreatin, pronase or a combination thereof.

5. A dialysis fluid according to claim 1, wherein the concentration of bicarbonate ions is from 20–40 meq/l.

6. A dialysis fluid according to claim 1, wherein the osmolality of the fluid is from about 100 to about 400 mOsm/Kg.

7. A dialysis fluid according to claim 1, wherein the pH is from about 6.6 to about 7.6.

8. A dialysis fluid according to claim 1, wherein the fluid is substantially free from glucose.

9. A dialysis fluid according to claim 1, which further contains physiological salts comprising ions selected from sodium, chloride, lactate, and citrate.

10. A dialysis fluid which is stable upon storage without precipitation and which has a pH of from about 6.6 to about 7.6 and a total osmolality of from about 100 to about 400 mOsm/Kg, said dialysis fluid comprising:
    i) an osmotic agent in an amount sufficient to contribute from about 25 to about 100 mOsm/Kg to the total osmolality of the dialysis fluid which comprises a mixture of peptides obtained by the action of one or more proteolytic enzymes on a phosphoprotein or mixture of phosphoproteins;
    ii) a buffering agent which comprises bicarbonate ions in an amount sufficient to give a concentration of bicarbonate ions in the dialysis fluid of from about 20 to about 40 meq/l; and
    iii) at least one cation selected from Ca2+ and Mg2+.

11. A dialysis fluid which is stable upon storage without precipitation and which has a pH of from about 6.6 to about 7.6 and a total osmolality of from about 100 to about 400 mOsm/Kg, said dialysis fluid comprising:
    i) an osmotic agent in an amount sufficient to contribute from about 25 to about 100 mOsm/Kg to the total osmolality of the dialysis fluid which comprises a mixture of peptides obtained by the action of at least one proteolytic enzyme on casein;
    ii) a buffering agent which comprises bicarbonate ions in an amount sufficient to give a concentration of bicarbonate ions in the dialysis fluid of from about 20 to about 40 meq/l; and
    iii) at least one cation selected from Ca2+ and Mg2+.

12. A dialysis fluid according to claim 11, wherein the casein comprises bovine casein.

13. A dialysis fluid according to claim 11, wherein the proteolytic enzyme comprises trypsin, chymotrypsin, pancreatin, pronase or a combination thereof.

14. A dialysis fluid according to claim 11, wherein the concentration of bicarbonate ions is from 20–40 meq/l.

15. A dialysis fluid according to claim 11, wherein the fluid is substantially free from glucose.

16. A dialysis fluid according to claim 11, which further contains physiological salts comprising ions selected from sodium, chloride, lactate, and citrate.

* * * * *